United States Patent
Azizian et al.

(10) Patent No.: US 12,167,943 B2
(45) Date of Patent: Dec. 17, 2024

(54) SYSTEM AND METHOD FOR AN ARTICULATED ARM BASED TOOL GUIDE

(71) Applicant: INTUITIVE SURGICAL OPERATIONS, INC., Sunnyvale, CA (US)

(72) Inventors: Mahdi Azizian, San Jose, CA (US); Andrew C. Waterbury, Sunnyvale, CA (US); Jonathan M. Sorger, Belmont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/308,992

(22) Filed: Apr. 28, 2023

(65) Prior Publication Data
US 2023/0338111 A1 Oct. 26, 2023

Related U.S. Application Data

(63) Continuation of application No. 16/813,120, filed on Mar. 9, 2020, now Pat. No. 11,666,413, which is a
(Continued)

(51) Int. Cl.
*A61B 90/50* (2016.01)
*A61B 1/00* (2006.01)
(Continued)

(52) U.S. Cl.
CPC .............. *A61B 90/50* (2016.02); *A61B 34/20* (2016.02); *A61B 90/11* (2016.02);
(Continued)

(58) Field of Classification Search
CPC ......... A61B 90/50; A61B 34/20; A61B 90/11; A61B 1/00149; A61B 34/25; A61B 34/70; B25J 9/009; B25J 9/1682
See application file for complete search history.

(56) References Cited

U.S. PATENT DOCUMENTS

| 4,386,602 A | 6/1983 | Sheldon et al. |
| 4,726,356 A | 2/1988 | Santilli et al. |

(Continued)

FOREIGN PATENT DOCUMENTS

EP 0653922 B1 * 12/1999

OTHER PUBLICATIONS

International Search Report and Written Opinion for Application No. PCT/US2015/058223, mailed on Feb. 1, 2016, 11 pages.
(Continued)

*Primary Examiner* — John Fitzgerald
*Assistant Examiner* — Tania Courson
(74) *Attorney, Agent, or Firm* — Haynes & Boone, LLP.

(57) ABSTRACT

A method of controlling a medical tool includes determining an insertion path and pose for the tool based on a target and deploying first and second articulated arms of a computer-assisted medical device based on a size and shape of a tool guide. The arms include respective pluralities of moveable links actuated by at least one respective actuator and forming respective kinematic chains extending from a base. The method further includes receiving the tool guide for coupling with the arms using respective mounting arms of the tool guide such that the tool guide functions as a link in a closed kinematic loop formed by joining the kinematic chains, orienting a guide hole of the tool guide to align with the insertion path, positioning the guide hole a desired distance away from the target, receiving the tool in the guide hole, and advancing the tool along the insertion path.

20 Claims, 5 Drawing Sheets

Related U.S. Application Data continuation of application No. 15/522,657, filed as application No. PCT/US2015/058223 on Oct. 30, 2015, now Pat. No. 10,603,135.

(60) Provisional application No. 62/072,612, filed on Oct. 30, 2014.

(51) Int. Cl.
    *A61B 34/00* (2016.01)
    *A61B 34/20* (2016.01)
    *A61B 90/11* (2016.01)
    *B25J 9/00* (2006.01)
    *B25J 9/16* (2006.01)

(52) U.S. Cl.
    CPC .......... *A61B 1/00149* (2013.01); *A61B 34/25* (2016.02); *A61B 34/70* (2016.02); *B25J 9/009* (2013.01); *B25J 9/1682* (2013.01)

(56) References Cited

U.S. PATENT DOCUMENTS

| | | | |
|---|---|---|---|
| 4,791,934 A | 12/1988 | Brunnett | |
| 5,129,911 A | 7/1992 | Siczek et al. | |
| 5,201,742 A * | 4/1993 | Hasson | A61B 90/11 606/1 |
| 5,343,391 A * | 8/1994 | Mushabac | A61C 9/008 433/79 |
| 5,397,323 A * | 3/1995 | Taylor | A61B 34/71 901/41 |
| 5,647,838 A | 7/1997 | Bloomer | |
| 5,797,835 A | 8/1998 | Green | |
| 5,931,832 A * | 8/1999 | Jensen | B25J 9/1065 606/1 |
| 5,966,991 A | 10/1999 | Gosselin et al. | |
| 6,070,109 A * | 5/2000 | McGee | B25J 9/1692 700/262 |
| 6,290,196 B1 | 9/2001 | Mayenberger | |
| 6,676,669 B2 | 1/2004 | Charles et al. | |
| 6,895,268 B1 | 5/2005 | Rahn et al. | |
| 7,155,316 B2 * | 12/2006 | Sutherland | A61B 34/37 901/1 |
| 7,559,935 B2 * | 7/2009 | Solar | A61B 90/11 606/130 |
| 7,744,608 B2 * | 6/2010 | Lee | A61B 34/20 606/1 |
| 7,818,044 B2 * | 10/2010 | Dukesherer | A61B 34/20 600/431 |
| 7,853,356 B2 * | 12/2010 | Tsai | B25J 9/1671 318/568.22 |
| 8,049,734 B2 * | 11/2011 | Rosenberg | A63F 13/2145 345/173 |
| 8,167,872 B2 | 5/2012 | Schena | |
| 8,216,211 B2 | 7/2012 | Mathis et al. | |
| 8,253,555 B2 | 8/2012 | Stevenson et al. | |
| 8,343,141 B2 | 1/2013 | Madhani et al. | |
| 9,089,256 B2 * | 7/2015 | Tognaccini | A61B 34/37 |
| 9,119,655 B2 * | 9/2015 | Bowling | A61B 34/10 |
| 9,138,129 B2 * | 9/2015 | Diolaiti | A61B 34/37 |
| 9,357,983 B2 | 6/2016 | Doyle | |
| 9,358,682 B2 * | 6/2016 | Ruiz Morales | A61B 34/77 |
| 9,398,934 B2 * | 7/2016 | Lee | A61B 34/30 |
| 9,498,297 B2 * | 11/2016 | Yousef | A61B 34/71 |
| 9,545,290 B2 | 1/2017 | Tellio et al. | |
| 9,566,122 B2 * | 2/2017 | Bowling | A61B 34/20 |
| 9,629,659 B2 | 4/2017 | Bhagat et al. | |
| 9,717,563 B2 * | 8/2017 | Tognaccini | A61B 1/04 |
| 10,300,268 B2 | 5/2019 | Skakoon et al. | |
| 10,314,661 B2 * | 6/2019 | Bowling | A61B 34/37 |
| 10,376,324 B2 | 8/2019 | Kerdok et al. | |
| 10,603,135 B2 | 3/2020 | Azizian et al. | |
| 10,617,479 B2 | 4/2020 | Itkowitz et al. | |
| 10,631,946 B2 * | 4/2020 | Loisel | A61B 90/10 |
| 10,758,695 B2 * | 9/2020 | Krimsky | A61M 27/00 |
| 10,765,306 B2 * | 9/2020 | Abou El Kheir | A61B 1/00029 |
| 10,905,497 B2 * | 2/2021 | Pandey | A61B 5/055 |
| 11,173,005 B2 * | 11/2021 | Azizian | A61B 34/35 |
| 11,576,737 B2 * | 2/2023 | Itkowitz | A61G 13/02 |
| 11,583,351 B2 * | 2/2023 | Kerdok | A61B 34/30 |
| 11,639,001 B2 * | 5/2023 | Bowling | A61B 34/10 700/254 |
| 11,648,112 B2 * | 5/2023 | Wallace | A61B 8/4477 623/2.11 |
| 11,666,413 B2 * | 6/2023 | Azizian | A61B 90/11 33/503 |
| 11,672,618 B2 * | 6/2023 | Itkowitz | A61B 34/30 700/250 |
| 11,684,448 B2 * | 6/2023 | Swarup | B25J 9/1689 700/245 |
| 11,737,842 B2 * | 8/2023 | Griffiths | A61B 34/30 700/248 |
| 11,744,598 B2 * | 9/2023 | Cameron | A61B 90/14 606/180 |
| 11,759,265 B2 * | 9/2023 | Griffiths | A61G 13/06 700/250 |
| 11,806,875 B2 * | 11/2023 | Swamp | B25J 9/1607 |
| 11,896,326 B2 * | 2/2024 | Itkowitz | A61B 34/25 |
| 2001/0009971 A1 | 7/2001 | Sherts et al. | |
| 2003/0055436 A1 * | 3/2003 | Daum | A61B 34/20 606/130 |
| 2007/0173975 A1 * | 7/2007 | Schena | A61B 34/70 700/245 |
| 2008/0004523 A1 | 1/2008 | Jensen | |
| 2008/0235970 A1 | 10/2008 | Crampton | |
| 2009/0326318 A1 * | 12/2009 | Tognaccini | A61B 34/37 600/109 |
| 2011/0010957 A1 | 1/2011 | Gomez et al. | |
| 2011/0046448 A1 | 2/2011 | Paolitto et al. | |
| 2012/0059392 A1 * | 3/2012 | Diolaiti | A61B 34/30 606/130 |
| 2013/0218137 A1 * | 8/2013 | Abovitz | A61B 34/70 606/1 |
| 2014/0012286 A1 * | 1/2014 | Lee | A61B 34/37 606/130 |
| 2014/0101953 A1 | 4/2014 | Briggs et al. | |
| 2014/0188132 A1 * | 7/2014 | Kang | A61B 6/4441 606/130 |
| 2016/0081754 A1 | 3/2016 | Kostrzewski et al. | |
| 2017/0014117 A1 * | 1/2017 | Capote | A61B 17/0206 |
| 2017/0079730 A1 * | 3/2017 | Azizian | A61B 34/35 |
| 2018/0184887 A1 * | 7/2018 | Abou El Kheir | A61B 1/3132 |
| 2018/0263597 A1 | 9/2018 | Tchang et al. | |
| 2019/0223972 A1 | 7/2019 | Fischer et al. | |
| 2019/0250384 A1 | 8/2019 | Themelis | |
| 2019/0328470 A1 * | 10/2019 | Tojo | A61B 34/25 |
| 2020/0100855 A1 * | 4/2020 | Leparmentier | A61B 1/3132 |
| 2020/0170732 A1 | 6/2020 | Patriciu | |
| 2020/0214790 A1 | 7/2020 | Azizian et al. | |
| 2020/0253595 A1 * | 8/2020 | McBride, Jr. | A61B 34/30 |
| 2022/0346810 A1 * | 11/2022 | Cameron | A61B 90/03 |
| 2023/0149104 A1 * | 5/2023 | Kerdok | A61B 90/57 606/130 |
| 2023/0190399 A1 * | 6/2023 | Spuhler | A61B 34/72 606/1 |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEM AND METHOD FOR AN ARTICULATED ARM BASED TOOL GUIDE

RELATED APPLICATIONS

This patent application is a continuation of U.S. patent application Ser. No. 16/813,120, filed Mar. 9, 2020 which is a continuation of U.S. patent application Ser. No. 15/522,657, filed Apr. 27, 2017 which is the U.S. national phase of International Application No. PCT/US2015/058223 filed Oct. 30, 2015 which claims priority to and the benefit of the filing date of U.S. Provisional Patent Application No. 62/072,612, entitled "SYSTEM AND METHOD FOR AN ARTICULATED ARM BASED TOOL GUIDE," filed Oct. 30, 2014, all of which are incorporated by reference herein in their entirety.

TECHNICAL FIELD

The present disclosure relates generally to operation of devices with articulated arms and more particularly to a tool guide for use with articulated arms.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held surgical instruments are being replaced by computer-assisted medical devices.

These electronic devices provide both advantages and challenges to the personnel operating them. Many of these electronic devices may be capable of autonomous or semi-autonomous motion of one or more articulated arms and/or end effectors. When the articulated arms and/or the end effectors include redundant degrees of freedom (i.e., more than the six degrees of freedom typically associated with Cartesian x, y, and z positioning and roll, pitch, and yaw orientations), the articulated arms and/or the end effectors may provide extensive flexibility in adjusting to changes in patient size, position, and/or orientation as the articulated arms and/or the end effectors are used to support medical procedures. This is possible because the redundant degrees of freedom allow the articulated arms and/or the end effectors to be positioned so as to avoid collisions among themselves, the patient, and/or other devices and personnel in an operating room and/or interventional suite.

Many medical procedures call for high precision in both the positioning and/or orientation of medical tools and/or devices. For example, medical procedures involving percutaneous ablation (including RF, cryo, microwave, and/or other forms of ablation), percutaneous needle biopsy, bone drilling, pedicle screw placement, seed planting, marker placement, medicine delivery, high magnification imaging, micro surgery, and/or the like often call for very precise control of not only the position of a device tool tip, but control over the orientation and/or advancement of the tool tip within a patient's anatomy.

Traditional approaches to the problem have relied on the skilled and steady hands of medical personnel operating a respective medical device. However, even the most skilled and steady of practitioners may not be able to ensure adequate placement and/or orientation of the medical device, especially, when significant force is used to advance the tool tip, such as when working in rigid anatomy, such as bones. Further, it may be difficult for the medical personnel to easily adjust to movements in the patient's anatomy and/or the patient or surgical table on which the patient is positioned.

Other approaches have relied on the use of tool jigs that are attached to the patient or surgical table, mounted on table-side stands, mounted to ceiling fixtures, and/or the like. Many of these tool jigs, however, may have limitations in their degrees of freedom, size, and/or the like that significantly limit their ability to be used with patients of different sizes, different positions within the anatomy of the patients, and/or with different procedures. These tool jigs may also have a limited ability to adapt to changes in patient position and/or orientation during a procedure. Additional flexibility may be obtained by using different tool jigs for different procedures, but the number of possible patients, positions, and/or procedures may involve an unacceptably large number of tool jigs.

Accordingly, it would be advantageous to develop systems and methods for using the flexibility of computer assisted articulated arms and/or end effectors to provide a tool guide for medical devices.

SUMMARY

Consistent with some embodiments, a tool guide for use with articulated arms includes an elongated body having a guide hole, a first joint attached to a first end of the body, a second joint attached to a second end of the body opposite the first end, a first mounting arm coupled to the body using the first joint, and a second mounting arm coupled to the body using the second joint. The first mounting arm is configured to be attached to a first articulated arm of a computer-assisted medical device. The second mounting arm is configured to be attached to a second articulated arm of the computer-assisted medical device. The guide hole is adapted to receive a medical tool and maintain a working end of the medical tool in alignment with the guide hole.

Consistent with some embodiments, a tool guide for use with articulated arms includes an elongated body, a joint attached to a first end of the body, a mounting arm coupled to the body using the joint, the mounting arm being configured to be attached to a first articulated arm of a computer-assisted medical device, and a tool sleeve attached to a second end of the body opposite the first end. The tool sleeve is adapted to receive an end effector attached to a second articulated arm of the computer-assisted medical device. The tool guide is adapted to provide greater precision in positioning and orienting the end effector.

Consistent with some embodiments, a computer-assisted medical device includes a control unit including one or more processors, a first articulated arm including one or more first joints, a second articulated arm including one or more second joints, and a tool guide. The tool guide includes an elongated body having a guide hole, a third joint attached to a first end of the body, a fourth joint attached to a second end of the body opposite the first end, a first mounting arm coupled to the body using the third joint and coupling the tool guide to a distal end of the first articulated arm, and a second mounting arm coupled to the body using the fourth joint and coupling the tool guide to a distal end of the second articulated arm. The guide hole is adapted to receive a working end of a medical tool. The control unit operates the first and second joints so as to position and align the guide hole in alignment with a target and steady the working end of the medical tool.

Consistent with some embodiments, a computer-assisted medical device includes a control unit including one or more processors, a first articulated arm including one or more first joints, a second articulated arm including one or more second joints, and a tool guide. The tool guide includes an elongated body, a third joint attached to a first end of the body, a mounting arm coupled to the body using the third joint and coupling the tool guide to a distal end of the first articulated arm, and a tool sleeve attached to a second end of the body opposite the first end. The tool sleeve is adapted to receive an end effector attached to the second articulated arm. The control unit operates the first joints to steady the end effector. And, the control unit operates the second joints to position and orient the end effector relative to a target.

Consistent with some embodiments, a method of controlling motion of a medical tool includes determining an insertion path and a pose for a medical tool based on a target, deploying first and second articulated arms of a computer-assisted medical device so that a distal end of each of the first and second articulated arms are positioned and oriented relative to each other based on a size and a shape of a tool guide, attaching the tool guide to first articulated arm and the second articulated arm using respective mounting arms of the tool guide, orienting a guide hole of the tool guide so as to align the guide hole with the insertion path, positioning the guide hole a desired distance away from the target based on the pose, placing the medical tool in the guide hole, and advancing the medical tool along the insertion path and toward the target.

Consistent with some embodiments, a method of controlling motion of a medical tool includes determining an insertion path and a pose for the medical tool based on a target, attaching a tool guide to a first articulated arm of a computer-assisted medical device using a mount of the tool guide, inserting an end effector of a second articulated arm of the computer-assisted medical device in a tool sleeve of the tool guide, positioning and orienting the tool sleeve based on the insertion path and the pose, attaching a second articulated arm to a mounting arm of the tool guide, advancing the end effector along the insertion path and toward the target, and steadying the end effector using the second articulated arm and the tool guide.

Consistent with some embodiments, a non-transitory machine-readable medium includes a plurality of machine-readable instructions which when executed by one or more processors associated with a medical device are adapted to cause the one or more processors to perform a method. The method includes determining an insertion path and a pose for a medical tool based on a target, deploying first and second articulated arms of a computer-assisted medical device so that a distal end of each of the first and second articulated arms are positioned and oriented relative to each other based on a size and a shape of a tool guide, attaching the tool guide to first articulated arm and the second articulated arm using respective mounting arms of the tool guide, orienting a guide hole of the tool guide so as to align the guide hole with the insertion path, positioning the guide hole a desired distance away from the target based on the pose, placing the medical tool in the guide hole, and advancing the medical tool along the insertion path and toward the target.

Consistent with some embodiments, a non-transitory machine-readable medium includes a plurality of machine-readable instructions which when executed by one or more processors associated with a medical device are adapted to cause the one or more processors to perform a method. The method includes determining an insertion path and a pose for the medical tool based on a target, attaching a tool guide to a first articulated arm of a computer-assisted medical device using a mount of the tool guide, inserting an end effector of a second articulated arm of the computer-assisted medical device in a tool sleeve of the tool guide, positioning and orienting the tool sleeve based on the insertion path and the pose, attaching a second articulated arm to a mounting arm of the tool guide, advancing the end effector along the insertion path and toward the target, and steadying the end effector using the second articulated arm and the tool guide.

Figure 1A:
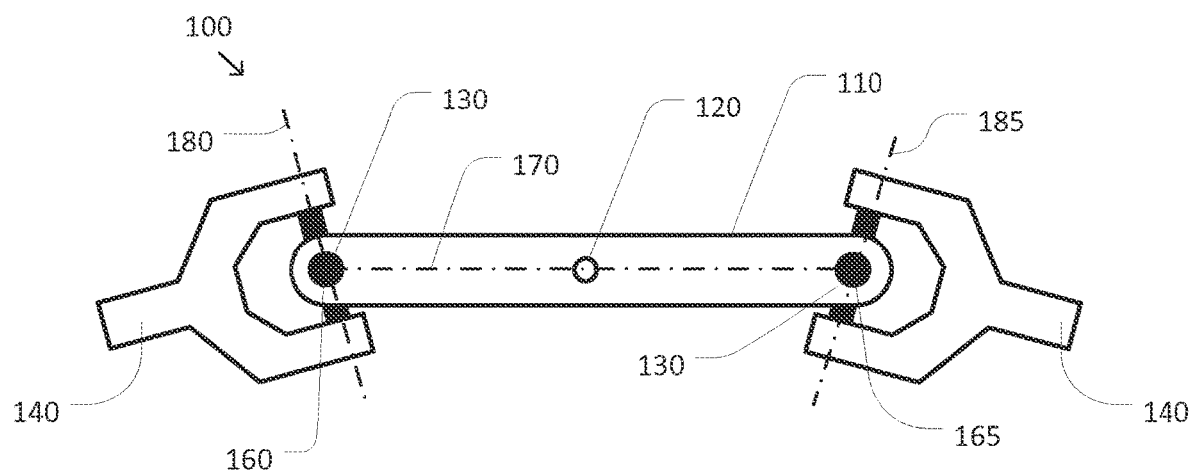
FIGS. 1A and 1B are simplified diagrams of a top and side view of a tool guide for use with two articulated arms and/or end effectors according to some embodiments.

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Computer-assisted systems with one or more articulated arms and/or end effectors provide great flexibility to the operating room and/or interventional suite. By providing computer control over the movement, position, and/or orientation of the articulated arms and/or the end effectors, it is possible for the computer-assisted system to provide significant advantages to both patients and medical personnel during medical procedures. In some examples, the computer-assisted systems may take advantage of information in both pre-operative and intra-operative images to help position and/or orient the end effectors and/or devices attached to the end effectors to desired positions within a patient's anatomy. In some examples, the computer-assisted systems may further provide guidance while a medical tool is being used during a procedure.

One possible use for a computer-assisted articulated arm and/or end effector is to act as a guide for a medical tool, which is being used during a procedure. In some examples, a tool guide may be attached in place of the end effector and/or at the end of the end effector. The tool guide may be used to aid medical personnel in the positioning, orientation, and/or use of an associated medical tool. In some examples, the medical tool may be suitable for percutaneous ablation including RF, cryo, microwave, and/or other forms of ablation), percutaneous needle biopsy, bone drilling, pedicle screw placement, seed planting, marker placement, medicine delivery, high magnification imaging, micro surgery, and/or the like.

In some embodiments, however, use of a single articulated arm and/or end effector with the tool guide may not provide adequate support for the associated medical tool. In some examples, the single articulated arm and/or end effector may not be able to provide sufficient stability while the associated medical tool is being operated. In some examples, the single articulated arm and/or end effector may have practical limits on the amount of force and/or torque that it may be able to apply to the associated medical tool. In some examples, the single articulated arm and/or end effector may have practical limits in positioning and/or orientation that may not be precise enough for the corresponding medical procedure. In some examples, the single articulated arm and/or end effector may also be subject to small oscillations and/or vibrations that may be undesirable.

In some embodiments, a tool guide attached to two separate articulated arms and/or end effectors may address many of the limitations of the single articulated arm and/or end effector tool guide. By attaching a tool guide to the ends of two separate articulated arms and/or end effectors, a closed kinematic chain through the two separate articulated arms and/or end effectors and the tool guide may be formed. In some examples, the closed kinematic chain may permit the computer-assisted system to obtain greater precision in position and/or orientation of the tool guide that would not otherwise be permitted with a single articulated arm and/or end effector. In some examples, the closed kinematic chain may also assist the two articulated arms and/or end effectors to position the tool guide with greater rigidity and/or stiffness. In some examples, the closed kinematic chain may also significantly reduce the small oscillations and/or vibrations of the two articulated arms and/or end effectors relative to a single articulated arm and/or end effector arrangement.

Figure 1B:
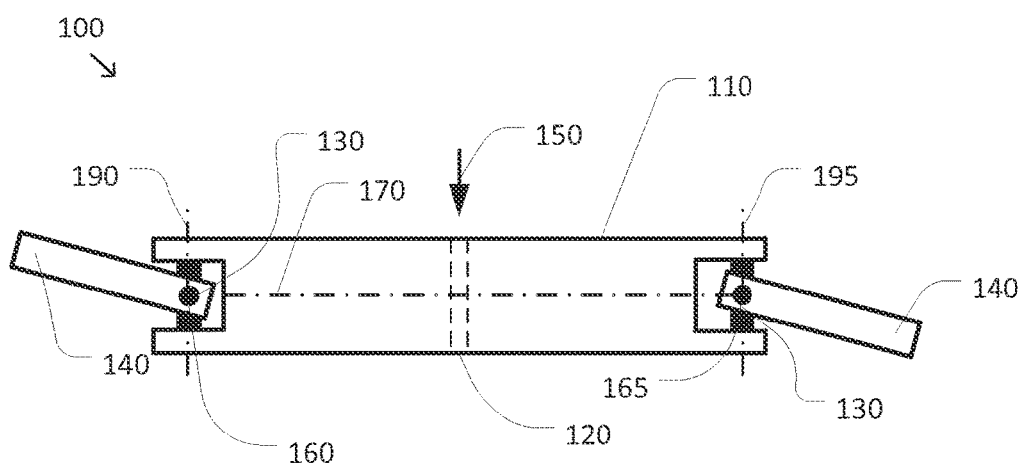

FIGS. 1A and 1B are simplified diagrams of a top and side view of a tool guide 100 for use with two articulated arms and/or end effectors according to some embodiments. As shown in FIGS. 1A and 1B, tool guide 100 includes a rigid or mostly rigid body 110 with an elongated shape. At some position along body 110, a guide hole 120 is provided for a medical tool. In some examples, guide hole 120 may be placed near a center of body 110 to help maximize the amount of clearance around guide hole 120 and between the two articulated arms and/or end effectors supporting tool guide 100. In some examples, guide hole 120 may have a diameter so as to provide a slip fit for the medical tool being guided by tool guide 100. In some examples, a thickness of body 110 in the axial direction of guide hole 120 (i.e., the direction of arrow 150) may be suitable to provide lateral stability to the medical tool being guided by tool guide 100. In some examples, the thickness of body 110 may be at least 1.5 cm in length and/or 3 cm in length or longer. Although not shown in FIGS. 1A and 1B, a bushing and/or elastomeric material may be inserted into guide hole 120 between body 110 and the medical tool to help reduce the transmission of vibrations from the medical tool to tool guide 110. And although, tool guide 100 is shown with only a single guide hole 120, additional guide holes may be included as appropriate for the medical tool being guided. Although the body 110 is shown to have an elongated shape, it may be shaped as a grid with a plurality of holes, which can be used for applications such as brachytherapy.

Tool guide 100 further includes joints 130 at ends of body 110 that couple body 110 to respective mounting arms 140. As shown in FIGS. 1A and 1B, the joints 130 include two degree of freedom universal joints allowing independent rotation of mounting arms 140 relative to body 110 along two separate axes. In some examples, the inclusion of the joints 130 adds additional degrees of freedom to a closed kinematic chain including tool guide 100. In some examples, these additional degrees of freedom may provide greater flexibility in positioning the articulated arms and/or end effectors that are holding tool guide 100 so as to increase the potential clearance between guide hole 120 and the articulated arms and/or end effectors. And although FIGS. 1A and 1B depict the joints 130 as two degree of freedom universal joints, other configurations are possible. In some examples, the joints 130 may be ball-in-socket joints. In some examples, the joints 130 may include zero and/or one degree of freedom and/or may include a more complex arrangement of joints and links providing for more than two degrees of freedom. In some examples, the joints 130 may be passive, may include varying levels of resistance to motion, and/or may include one or more actuators making them active joints. In some embodiments, the joints 130 may include one or more sensors for determining a position, orientation, force, and/or torque of the joints 130. In some examples either of the joints 130 may be lockable (e.g., by a manually-tightened friction feature) to temporarily prevent the respective joint 130 from moving. In some embodiments, the joints 130 may benefit from a variable stiffness joint mechanism using materials and techniques such as electro-rheological (ER) and/or magneto-rheological (MR) fluids.

In some embodiments, mounting arms 140 may include one or more features to help support use of tool guide 100 with the articulated arms and/or end effectors. In some examples, the ends of mounting arms 140 opposite the joints 130 may include a standardized attachment arrangement designed to mate with specific articulated arms and/or end effectors—such as a standardized structure used to mount a cannula and/or a guide tube on a single articulated arm. In some examples, the standardized attachment may provide a rigid, non-slip attachment between tool guide 100 and the articulated arms and/or end effectors. In some examples, mounting arms 140 may include one or more notches, flanges, clips, and/or the like suitable for attaching each of the mounting arms 140 to a respective articulated arm and/or end effector. In some examples, by attaching tool guide 100 to the articulated arms using the mounting arms 140, tool guide 100 becomes a shared end effector for the articulated arms. In some examples, mounting arms 140 may each include suitable identifying features so the articulated arm and/or end effector to which the mounting arm 140 is attached may identify the mounting arm 140 as belonging to tool guide 100 and may further identify a model number of tool guide 100. In some examples, the identifying features may include one or more physical patterns, electrical contacts, magnets, RFID devices, and/or the like. In some examples, mounting arms 140 may further include electrical and/or physical contacts for allowing the articulated arms and/or end effectors to read the sensors and/or command the actuators in the joints 130.

The configuration of tool guide 100 may be used to determine a kinematic model that may be used to describe the constrained kinematic relationship between the articulated arms and/or end effectors holding tool guide 100. The kinematic model of tool guide 100 is subject to the following constraints: (1) a fixed length of body 110 between pivot points 160 and 165, along the axis 170, (2) body 110 may not be twisted, therefore the rotation angle around axis 170 should be the same at both pivot points 160 and 165, (3) angles around axes 180 and 190 at pivot point 160 and angles around axes 185 and 195 at pivot point 165 should be within corresponding joint limits of joints 130. These kinematic constraints on tool guide 100 pose 6 equations, which uniquely determine the relationship between coordinate frames of the articulated arms and/or end effectors holding tool guide 100.

In some embodiments, tool guide 100 may further include a memory device (not shown). In some examples, the memory device may be used to store information associated with tool guide 100 including tool guide type, tool guide identification number, tool guide model number, tool guide kinematic parameters, and/or the like. In some examples, the stored information may be read by the computer-assisted system upon connection of either of the mounting arms 140 to one of the articulated arms and/or one of the end effectors. In some examples, the read information may be used by the computer-assisted system to identify tool guide 100, set control parameters, access the kinematic parameters, and/or the like. In some examples, the memory device may be accessed using the electrical contacts, RF communication, and/or the like. In some examples, the memory device may include a machine readable media, such as RAM, PROM, EPROM, FLASH-EPROM, any other memory chip or cartridge, and/or any other medium from which a processor or computer is adapted to read.

In some embodiments, the mounting arms 140 may be used to provide electrical power to tool guide 100. In some examples, the electrical power may be used to operate the sensors, drive the actuators, control stiffness of the joints 130 via ER and/or MR fluids, and/or the like.

According to some embodiments, while tool guide 100 is in use, guide hole 120 may be positioned above target anatomy of a patient and aligned so that the axial direction of guide hole 120 is aligned to the target anatomy. Once in position and alignment, the medical tool may be inserted through guide hole 120 in the direction indicated by arrow 150. In some examples, a working end (such as a needle, drill bit, tube, shaft, and/or other element) of the medical tool may be inserted through guide hole 120 in the direction of arrow 150 so that the working end is maintained in alignment with the target anatomy. In some examples, body 110 of tool guide 100 may also act as a stop for the medical tool that prohibits at least some portion of the medical tool, larger than guide hole 120 from advancing beyond body 110.

Figure 2:
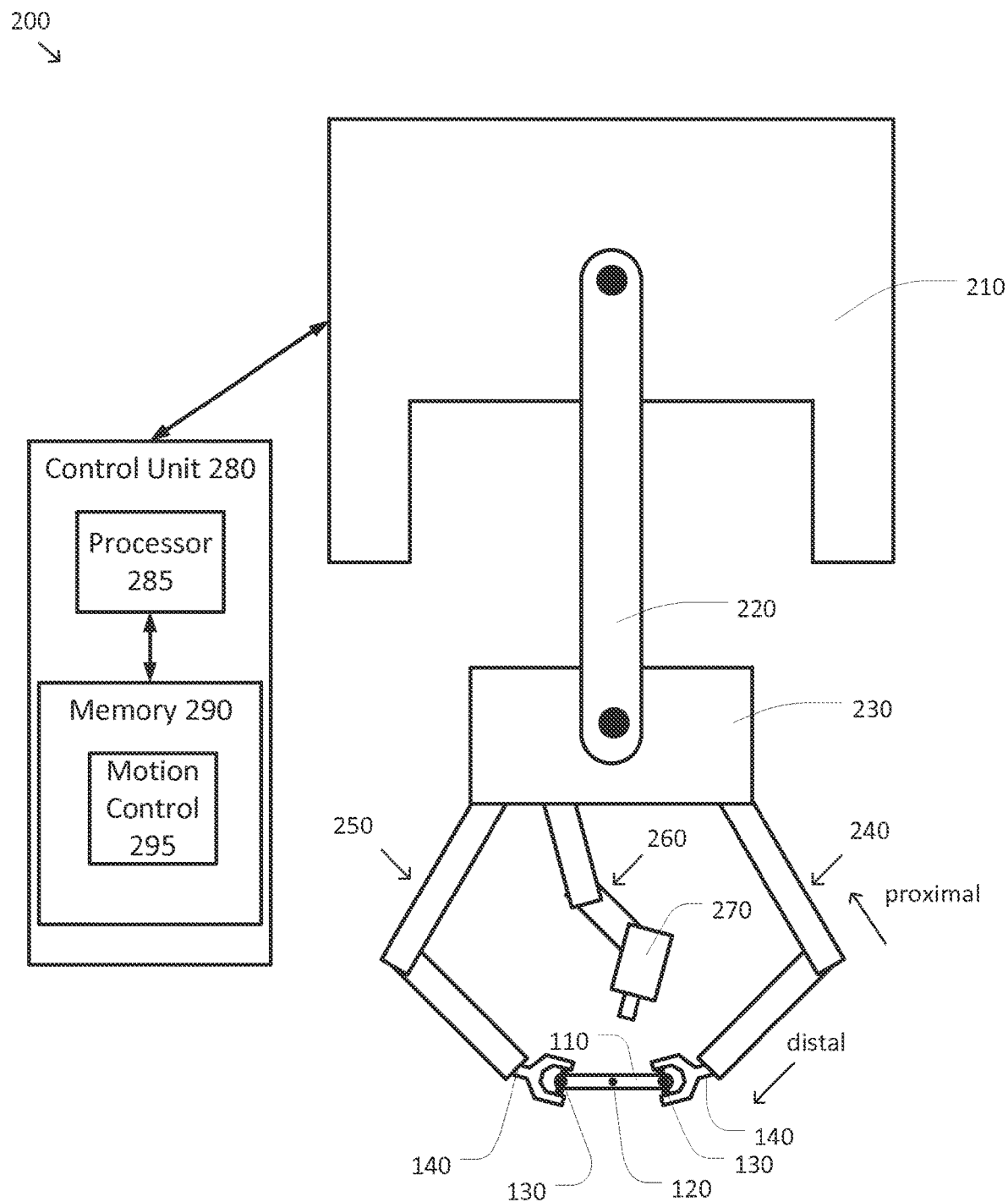
FIG. 2 is a simplified diagram of a computer-assisted system according to some embodiments.

FIG. 2 is a simplified diagram of a computer-assisted system 200 according to some embodiments. As shown in FIG. 2, computer-assisted system 200 includes a computer-assisted medical device supporting multiple articulated arms. In some embodiments, the computer-assisted medical device and an operator workstation (not shown) may correspond to a da Vinci® Surgical System commercialized by Intuitive Surgical, Inc. of Sunnyvale, California. The computer-assisted medical device includes a base 210. In some examples, base 210 may include one or more wheels and/or may be mounted on a track to facilitate positioning of the computer-assisted medical device within an operating room, interventional suite, and/or adjacent to a patient table. To facilitate positioning of the articulated arms of the computer-assisted medical device, a set-up structure 220 may be mounted on base 210. The set-up structure 220 may include one or more joints and/or links that may be used to adjust a position, orientation, and/or height of an articulated arm gantry 230. In some examples, gantry 230 may be positioned over a patient table. In some examples, set-up structure 220 may further include one or more sensors and/or the like to allow computer-assisted system 200 to determine a forward and/or inverse kinematic transform characterizing the position and/or orientation of gantry 230 relative to base 210. In some examples, set-up structure 220 may further include one or more actuators and/or the like to allow computer-assisted system 200 to change the position and/or orientation of gantry 230 relative to base 210 and set-up structure 220.

Attached to gantry 230 are several articulated arms 240, 250, and 260. And although FIG. 2 shows three articulated arms 240, 250, and 260 attached to gantry 230, other configurations may include only two articulated arms, and additional articulated arms may also be present. Each of the articulated arms 240, 250, and 260 may include one or more joints and links between the proximal end attached to gantry 230 and the distal end to which a respective end effector, tool, imaging device, tool guide, medical tool, and/or the like are attached. In some examples, each of the articulated arms 240, 250, and 260 may further include one or more sensors and/or the like to allow computer-assisted system 200 to determine a forward and/or inverse kinematic transform characterizing the position and/or orientation of the distal end of the respective articulated arm 240, 250, and/or 260 relative to gantry 230. In some examples, each of the articulated arms 240, 250, and 260 may further include one or more sensors for determining forces and/or torques being applied to the joints and/or links of the respective articulated arm 240, 250, and/or 260. In some examples, each of the articulated arms 240, 250, and 260 may further include one or more actuators and/or the like to allow computer-assisted system 200 to change the position and/or orientation of respective end effectors at the distal ends of each of the articulated arms 240, 250, and 260 relative to gantry 230.

As shown in FIG. 2, a first mounting arm 140 of a tool guide is attached to the distal end of articulated arm 240 and a second mounting arm 140 of the tool guide is attached to the distal end of articulated arm 250. The resulting structure creates a closed kinematic loop between gantry 230, through articulated arm 240, the mounting arms 140, joints 130, and body 110 of the tool guide, through articulated arm 250, and back to gantry 230. In some examples, the closed kinematic loop may be used to provide stability in the position and/or orientation of guide hole 120 over target anatomy of a patient. In some examples, the closed kinematic loop may be used to provide higher stiffness for the tool guide 100 relative to the stiffness of a single articulated arm approach.

As further shown in FIG. 2, an imaging device 270 may be attached to the distal end of articulated arm 260. In some examples, imaging device 270 may be an endoscope, an ultrasound device, and/or the like. In some examples, imaging device 270 may provide one or more images of the target anatomy to facilitate the use of a medical tool inserted through guide hole 120. In some examples, when imaging device 270 includes stereoscopic and/or other three-dimensional imaging capabilities, imaging device 270 may be used to determine a kinematic relationship between gantry 230 and the target anatomy. In some examples, this kinematic relationship may be useful in positioning and/or orienting guide hole 120 and the tool guide relative to the target anatomy.

The computer-assisted medical device is coupled to a control unit 280 via an interface. The interface may include one or more cables, connectors, and/or buses and may further include one or more networks with one or more network switching and/or routing devices. Control unit 280 includes a processor 285 coupled to memory 290. Operation of control unit 280 is controlled by processor 285. And although control unit 280 is shown with only one processor 285, it is understood that processor 285 may be representative of one or more central processing units, multi-core processors, microprocessors, microcontrollers, digital signal processors, field programmable gate arrays (FPGAs), application specific integrated circuits (ASICs), and/or the like in control unit 280. Control unit 280 may be implemented as a stand-alone subsystem and/or board added to a computing device or as a virtual machine. In some embodiments, control unit 280 may be included as part of an operator workstation (not shown) for allowing medical personnel to control and/or operate computer-assisted system 200. In some examples, control unit 280 may be operated separately from, but in coordination with the operator workstation.

Memory 290 may be used to store software executed by control unit 280 and/or one or more data structures used during operation of control unit 280. Memory 290 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 290 includes a motion control application 295 that may be used to support autonomous and/or semiautonomous control of computer-assisted system 200. Motion control application 295 may include one or more application programming interfaces (APIs) for receiving position, motion, and/or other sensor information from the sensors in set-up structure 220, the articulated arms 240, 250, and/or 260, and/or the tool guide as will be discussed in further detail below. In some examples, motion control application 295 may receive one or more pre-operative images, intra-operative images, images from imaging device 270, and/or the like as will be discussed in further detail below. In some examples, motion control application 295 may support the autonomous and/or semi-autonomous motion of articulated arms 240, 250, and/or 260 to help position and/or orient the tool guide as will be discussed in further detail below. In some examples, motion control application 295 may also exchange position, motion, and/or collision avoidance information with other control units regarding other devices, and/or planning and/or assisting in the planning of motion for computer-assisted system 200, articulated arms 240, 250, and/or 260, and/or the like. And although motion control application 295 is depicted as a software application, motion control application 295 may be implemented using hardware, software, and/or a combination of hardware and software.

Figure 3:
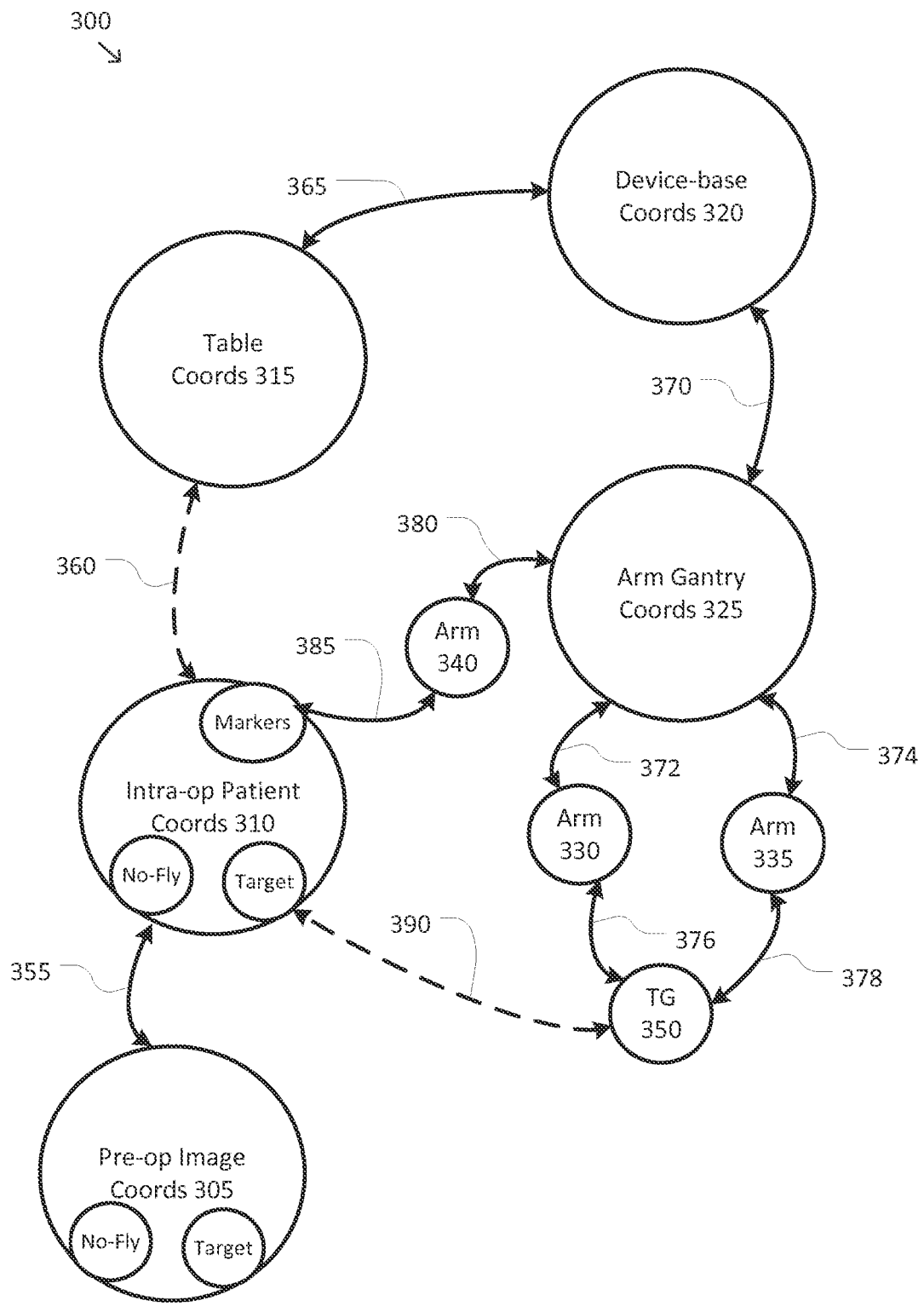
FIG. 3 is a simplified diagram of a kinematic model of a computer-assisted medical system according to some embodiments.

FIG. 3 is a simplified diagram of a kinematic model 300 of a computer-assisted medical system according to some embodiments. As shown in FIG. 3, kinematic model 300 may include kinematic information associated with many sources and/or devices. In some embodiments, before a medical procedure is performed, it is common for one or more pre-operative images to be obtained. In some examples, these pre-operative images may include a series of tomographic images that may be used to develop a three-dimensional model of the patient's anatomy. In some examples, the pre-operative images may be taken via computed tomography (CT), magnetic resonance imaging (MRI), and/or the like. In some examples, medical personnel may review the pre-operative images to develop a plan for a medical procedure that may identify one or more targets (e.g., positions for needle ablation, biopsy, seed positions, drilling points, pedicle screw positions, and/or the like). In some examples, the plan may also identify one or more no-fly zones that may be used to protect patient anatomy during the medical procedure. In some examples, the pre-operative images, as well as the targets and/or no-fly zones may be established in a pre-operative image coordinate system 305. In some examples, the pre-operative image coordinate system 305 may be determined in part by a coordinate system and/or one or more kinematic models associated with the one or more imaging devices taking the pre-operative images.

In some embodiments, once the patient is positioned and oriented for the medical procedure, one or more intra-operative images may be obtained to determine the position and/or orientation of the patient for the medical procedure. In some examples, the intra-operative images may include two or more x-rays obtained along non-parallel axes. In some examples, the non-parallel axes may have an angular separation of at least 30 degrees. In some examples, the x-ray images may be lateral and anterior-posterior images of the patient. In some examples, the intra-operative images may use other imaging technology that identifies three-dimensional information and may include ultrasound, bi-plane fluoroscopy, stereoscopic fluorescence imaging, and/or the like. In some examples, an intra-operative patient coordinate system 310 may be determined in part by a coordinate system and/or one or more kinematic models associated with the one or more imaging devices taking the intra-operative images.

In some embodiments, medical personnel may review the intra-operative images to determine positions of the targets identified as part of the plan using the pre-operative images. In some examples, one or more no-fly zones may also be identified in the intra-operative images. In some examples, positions of one or more markers and/or identified anatomical features may be located using the intra-operative images. In some examples, the intra-operative images, as well as the targets, no-fly zones, features, and/or markers may be established in the intra-operative patient coordinate system 310.

In some embodiments, the patient may be located on a patient table that may be positioned and/or oriented by medical personnel. In some examples, a height of the patient table above the floor may be adjusted. In some examples, an orientation of the patient table may be adjusted along one or more roll, pitch, yaw, and/or the like axes. In some examples, the position and/or orientation of the patient table may be established in a table coordinate system 315.

In some embodiments, a computer-assisted medical device, such as the computer-assisted medical device of FIG. 2, may be used during the medical procedure. In some examples, the position and/or orientation of a base of the computer-assisted medical device may be adjusted relative to the patient table. In some examples, the computer-assisted medical device may be established in a device-base coordinate system 320.

In some embodiments, the computer-assisted medical device may include a set-up structure, such as set-up structure 220, to adjust a position and orientation of a gantry to which one or more articulated arms are attached. In some examples, the gantry may be similar to gantry 230. In some examples, the gantry may be established in an arm gantry coordinate system 325.

In some embodiments, a plurality of articulated arms may be attached to the gantry. Each of the articulated arms may include one or more joints and/or links with the joints and/or links establishing a coordinate system 330, 335, and/or 340 at a distal end of each of the articulated arms and/or an end effector at the distal end of a respective articulated arm. In some examples, the articulated arms associated with arm coordinate systems 330 and 335 may correspond to articulated arms 240 and 250 and the articulated arm associated with arm coordinate system 340 may correspond to articulated arm 260.

In some embodiments, a tool guide, such as tool guide 100, may be coupled between the articulated arms associated with arm coordinate systems 330 and 335. In some examples, the tool guide and/or a guide hole of the tool guide may be established in a tool guide coordinate system 350.

In some embodiments, an imaging device may be coupled to the distal end of the articulated arm associated with arm coordinate system 340. In some examples, the imaging device may be an endoscope, an ultrasound device, a microscope, and/or the like. In some examples, the imaging device may include stereoscopic and/or other three-dimensional positioning capabilities for mapping observed images to arm coordinate system 340.

In some embodiments, kinematic modeling and/or one or more registration processes may be used to establish the kinematic relationships between the various coordinate systems 305-350. In some examples, the kinematic modeling and/or registration processes may be used to establish transformation matrices between the various coordinate systems 305-350 to permit the forward and/or reverse mapping of positions and/or orientations in one of the coordinate systems 305-350 to another of the coordinate systems 305-350.

In some embodiments, a registration process may be used to determine a pre-operative to intra-operative kinematic relationship 355 between the pre-operative coordinate system 305 and the intra-operative patient coordinate system 310. In some examples, the registration process may include identifying common image elements in the pre-operative and intra-operative images (e.g., unique and/or unusual anatomical features, markers, and/or the like), locating the common image elements in both the pre-operative image and intra-operative patient coordinate systems 305, 310, and using the differences between the positions and/or orientations of the common image elements to determine the translations, scales, and/or rotations between the pre-operative image coordinate system 305 and the intra-operative coordinate system 310. The translations, scales, and/or rotations may be used to determine the pre-operative to intra-operative kinematic relationship 355. In some examples, the pre-operative to intra-operative kinematic relationship 355 may be used to transform the targets and/or no-fly zones identified during the pre-operative plan from the pre-operative image coordinate system 305 to the intra-operative patient coordinate system 310. In some examples, the pre-operative to intra-operative kinematic relationship 355 may include multiple transformations that apply to sub-regions within the pre-operative and intra-operative coordinate systems 305 and 310 to account for changes in the patient's anatomy between a pose used for the pre-operative images and the pose used for the intra-operative images. In some examples, the sub-regions may account for changes in positions of the patient's joints, vertebrae, and/or the like between the pre-operative and intra-operative poses.

In some embodiments, a patient to table kinematic relationship 360 between the patient (i.e., the intra-operative patient coordinate system 310) and the patient table (i.e., the table coordinate system 315) may not be directly determined. However, a closed kinematic chain may be used to determine the patient to table kinematic relationship 360 as is discussed in further detail below.

In some embodiments, a table to device-base kinematic relationship 365 may be determined using a registration process between the patient table and the computer-assisted medical device. Methods and approaches for establishing the table to device-base kinematic relationship are described in greater detail in U.S. Patent Application No. 61/954,538 (filed Mar. 17, 2014) (entitled "Methods and Systems for Tele-Surgical Table Registration"), which is hereby incorporated by reference for all purposes.

In some embodiments, a set-up structure kinematic relationship 370 between the device-base coordinate system 320 and the arm gantry coordinate system 325 may be determined by using one more kinematic models of the set-up structure coupling the device base to the gantry. In some examples, one or more sensors located in the set-up structure may be used to determine the coordinate transformation associated with the set-up structure kinematic relationship 370. In some examples, the set-up structure kinematic relationship 370 may be updated as the gantry is moved to different positions and/or orientations relative to the device base coordinate system 320.

In some embodiments, corresponding articulated arm kinematic relationships 372 and 374 between the arm gantry coordinate system 325 and the articulated arm coordinate systems 330 and 335, respectively, may be determined by using one or more kinematic models of the articulated arms and/or end effectors coupling the gantry to a distal end of the corresponding articulated arms and/or end effectors. In some examples, one or more sensors located in the articulated arms and/or end effectors may be used to determine the coordinate transformation associated with the corresponding articulated arm kinematic relationships 372 and 374. In some examples, the articulated arm kinematic relationships 372 and 374 may be updated as the articulated arms and/or end effectors are moved to different positions and/or orientations relative to the arm gantry coordinate system 325.

In some embodiments, corresponding tool guide kinematic relationships 376 and 378 between the respective arm coordinate systems 330 and 335 and the tool guide coordinate system 350 may be determined by using the closed kinematic loop through the tool guide and the kinematics of the joints (e.g., joints 130) and body (e.g., body 110) of the tool guide. Even when the joints of the tool guide are passive and may not have joint actuators, the closed kinematic loop of the two articulated arms coupled to the tool guide permits determination of the tool guide kinematic relationships 376 and 378. In some examples, the articulated arm kinematic relationships 372 and 374 may be used to determine a position and an orientation of the connection points of the tool guide to both of the articulated arms in the same articulated arm coordinate system 330 or 335. Consider the case where the tool guide 100 is attached to articulated arms 240 and 250 with corresponding coordinate systems 330 and 335. In order to determine the kinematic relationships 376 and 378, the constrained kinematic equation between coordinate systems 330 and 335 may be solved in such a way that it satisfies the following conditions: (1) a fixed length of body 110 between pivot points 160 and 165, along axis 170, (2) body 110 may not be twisted, therefore the rotation angle around axis 170 should be the same at both pivot points 160 and 165, (3) angles around axes 180 and 190 at pivot point 160 and angles around axes 185 and 195 at pivot point 165 should be within corresponding joint limits of joints 130. These constraints pose 6 equations, which uniquely determine the coordinate frame 350 given the coordinate frames 330 and 335, which are known from forward kinematic models of the arms 240 and 250; by solving these equations, kinematic relationships 376 and 378 between coordinate frames 330 and 350 and between coordinate frames 335 and 350 may be determined.

In some embodiments, an articulated arm kinematic relationship 380 between the arm gantry coordinate system 325 and the articulated arm coordinate system 340 may be determined by using one or more kinematic models of the articulated arm and/or end effector coupling the gantry to a distal end of the articulated arm and/or end effector. In some examples, one or more sensors located in the articulated arm and/or end effector may be used to determine the coordinate transformation associated with the articulated arm kinematic relationship 380. In some examples, the articulated arm kinematic relationship 380 may be updated as the articulated arm and/or end effector are moved to a different position and/or orientation relative to the gantry coordinate system 325.

In some embodiments, when an imaging device coupled to the articulated arm associated with the articulated arm coordinate system 340 is able to observe the features and/or markers located in the intra-operative patient coordinate system 310, it is possible to determine a patient kinematic relationship 385 between the articulated arm coordinate system 340 and the anatomy of the patient. In some examples, image processing of one or more images obtained by the imaging device may be used to determine positions and/or orientations of the features and/or markers on the anatomy of the patient in articulated arm coordinate system 340 and, thus, determine the patient kinematic relationship 385. In some examples, the positions and/or orientations of the targets and no-fly zones regions in the intra-operative patient coordinate system 310 may be mapped to the articulated arm coordinate system 340 by using the patient kinematic relationship 385.

In some embodiments, a closed kinematic chain through the intra-operative patient coordinates 310, patient kinematic relationship 385, articulated arm coordinate system 340, articulated arm kinematic relationship 380, arm gantry coordinate system 325, one of the articulated arm kinematic relationships 372 or 374, a corresponding one of the articulated arm coordinate systems 330 or 335, a corresponding one of the tool guide kinematic relationships 376 or 378, and the tool guide coordinate system 350 may be used to determine a tool to target kinematic relationship 390 by suitable application of the inverse and forward kinematic relationships. In some examples, the tool to target kinematic relationship 390 may be used to quickly convert the position and orientation of the guide hole of the tool guide in the tool guide coordinate system 350 to the intra-operative patient coordinate system 310 so as to effectively control the alignment of the guide hole with the target while providing an insertion axis which may avoid the no-fly zones.

In some embodiments, the patient to table kinematic relationship 360 may also be determined using the closed kinematic loop through the table to device-base kinematic relationship 365, the set-up kinematic relationship 370, the articulated arm kinematic relationship 380, and the patient kinematic relationship 385.

In some embodiments, the various kinematic relationships 355-390 may also be used to support collision avoidance when using the computer-assisted medical device. In some examples, the kinematic relationships (e.g., kinematic relationships 372, 374, 376, 378, and/or 380) may be used to help avoid collisions between the various articulated arms, such as between the articulated arms holding the tool guide and the articulated arm holding the imaging device used to establish the patient kinematic relationship 385. In some examples, the kinematic relationships (e.g., kinematic relationships 360-390) may be used to prevent the articulated arms from entering the no-fly zones in the intra-operative patient coordinate system 310 and/or the patient table.

Figure 4:
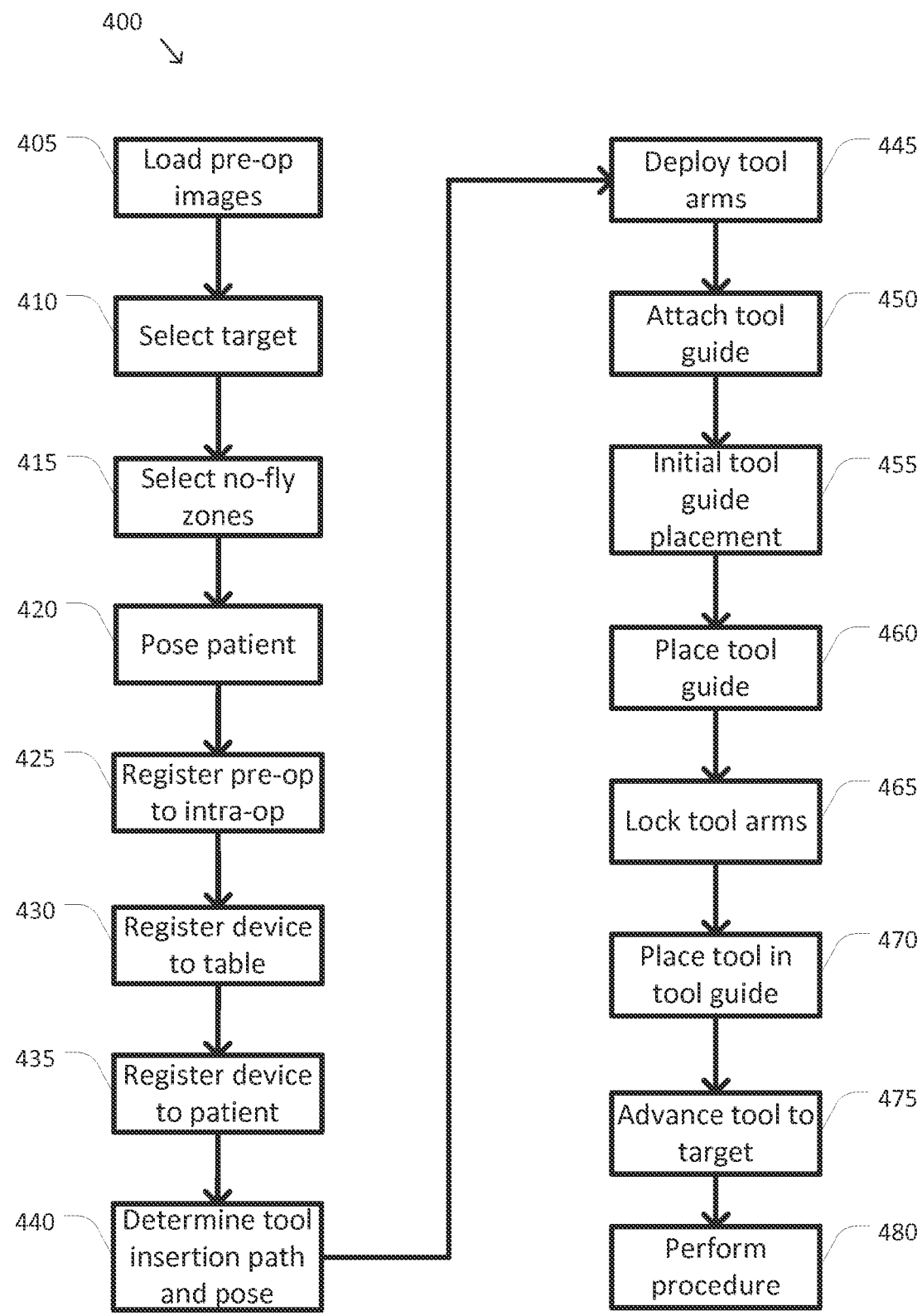
FIG. 4 is a simplified diagram of a method of tool guide use according to some embodiments.

FIG. 4 is a simplified diagram of a method 400 of tool guide use according to some embodiments. One or more of the processes 405-480 of method 400 may be implemented, at least in part, in the form of executable code stored on non-transient, tangible, machine readable media that when run by one or more processors (e.g., the processor 285 in control unit 280) may cause the one or more processors to perform one or more of the processes 405-480. In some embodiments, the method 400 may be performed by an application, such as motion control application 295. In some embodiments, processes 415, 430, and/or 455 are optional and may be omitted.

At a process 405, one or more pre-operative images are loaded. In some embodiments, a surgical plan is determined upon review of the one or more pre-operative images. In some examples, the one or more pre-operative images may be images of a desired portion of a patient's anatomy. In some examples, the one or more pre-operative images may include one or more slices and/or other three-dimensional information of the patient's anatomy. In some examples, the one or more pre-operative images may be obtained from a tomographic imaging device such as a CT, MRI, and/or similar imaging device. In some examples, the one or more pre-operative images may be associated with a pre-operative image coordinate system, such as pre-operative image coordinate system 305. During process 405, at least one of the pre-operative images is loaded for display to medical personnel.

At a process 410, a target is selected. In some embodiments, the medical personnel may review the one or more pre-operative images loaded during process 405 to determine a target for a medical procedure. In some examples, the target may be selected using a pointing device on the pre-operative image loaded during process 405. In some examples, the target may be associated with a portion of a patient's anatomy that is to be the subject of percutaneous ablation including RF, cryo, microwave, and/or other forms of ablation), percutaneous needle biopsy, bone drilling, pedicle screw placement, seed planting, marker placement, medicine delivery, high magnification imaging, micro surgery, and/or the like. In some examples, the target may be located within the pre-operative image coordinate system.

At an optional process 415, one or more no-fly zones are selected. In some embodiments, the medical personnel may further review the one or more pre-operative images loaded during process 405 to determine one or more no-fly zones within the one or more pre-operative images. In some examples, the one or more no-fly zones may be selected using a pointing device on the pre-operative image loaded during process 405. In some examples, the one or more no-fly zones may correspond with one or more regions of the patient's anatomy, which are to be avoided by a computer-assisted surgical system and/or one or more medical tools. In some examples, the one or more no-fly zones may be located within the pre-operative image coordinate system.

At a process 420, the patient is posed. In some embodiments, the patient may be prepared for a medical procedure and then posed on a patient table. In some examples, once the patient is posed, the particular pose may be associated with an intra-operative patient coordinate system, such as intra-operative patient coordinate system 310. In some examples, the patient table may be associated with a table coordinate system, such as table coordinate system 315.

At a process 425, the one or more pre-operative images are registered to one or more intra-operative images. In some embodiments, once the patient is posed for the medical procedure during process 420, one or more intra-operative images may be obtained to determine the position and/or orientation of the patient for the medical procedure. In some examples, the intra-operative images may include two or more x-rays obtained along non-parallel axes. In some examples, the non-parallel axes may have an angular separation of at least 30 degrees. In some examples, the x-ray images may be lateral and anterior-posterior images of the patient. In some examples, the intra-operative images may use other imaging technology that identifies three-dimension information and may include ultrasound, bi-plane fluoroscopy, stereoscopic fluorescence imaging, and/or the like. In some examples, the one or more intra-operative images may be associated with the intra-operative patient coordinate system.

In some examples, the registration may be used to determine a pre-operative to intra-operative kinematic relationship, such as the intra-operative kinematic relationship 355 between the pre-operative coordinate system 305 and the intra-operative patient coordinate system 310. In some examples, the registration process may include automated and/or semi-automated identification of one or more common image elements in the one or more pre-operative images and the one or more intra-operative images (e.g., one or more unique and/or unusual anatomical features, markers, and/or the like), locating the one or more common image elements in both the pre-operative image and intra-operative patient coordinate systems, and using the differences between the positions and/or orientations of the one or more common image elements to determine the translations, scales, and/or rotations between the pre-operative image coordinate system and the intra-operative patient coordinate system. The translations, scales, and/or rotations may be used to determine the pre-operative to intra-operative kinematic relationship. In some examples, the pre-operative to intra-operative kinematic relationship may be used to transform the target selected during process 410 and/or the one or more no-fly zones selected during process 415 from the pre-operative image coordinate system to the intra-operative patient coordinate system. In some examples, the user may update the target position and/or the no-fly zones based on the intra-operative patient pose. In some examples, the pre-operative to intra-operative kinematic relationship may include multiple transformations that apply to sub-regions within the pre-operative and intra-operative coordinate systems to account for changes in the patient's anatomy between a pose used for the one or more pre-operative images loaded during process 405 and the pose used for the one or more intra-operative images. In some examples, the sub-regions may account for changes in positions of the patient's joints, and/or the like between the pre-operative and intra-operative poses.

At an optional process 430, a computer-assisted medical device is registered to the patient table. In some embodiments, a table to medical device kinematic relationship, such as the table to device-base kinematic relationship 365, may be determined using a registration process between the patient table and the computer-assisted medical device. Methods and approaches for establishing the table to medical device kinematic relationship are described in greater detail in U.S. Patent Application No. 61/954,538, incorporated by reference above.

At a process 435, the computer-assisted medical device is registered to the patient. In some embodiments, registering of the computer-assisted medical device with the patient may begin with the acquisition of one or more computer-assisted medical device based images. The one or more computer-assisted medical device based images may be obtained to determine the position and/or orientation of the patient relative to the computer-assisted medical device. In some examples, the one or more computer-assisted medical device based images may be obtained by using an imaging device mounted on the computer-assisted medical device. In some examples, the one or more computer-assisted medical device based images may be obtained using imaging device 270 mounted at the distal end of an articulated arm (e.g., articulated arm 260) of the computer-assisted medical device. In some examples, the image device may be an endoscope, an ultrasound device, and/or the like. In some examples, the one or more computer-assisted medical device based images may provide one or more images of the patient's anatomy associated with one or more features and/or targets with known coordinates in the intra-operative patient coordinate system.

In some examples, the registration may be used to determine a patient to computer-assisted medical device kinematic relationship, such as the patient kinematic relationship 385 between the intra-operative coordinate system 310 and the articulated arm coordinate system 340. In some examples, the registration process may include automated and/or semi-automated identification of the one or more features and/or targets in the one or more computer-assisted medical device based images and the one or more intra-operative and/or one or more pre-operative images and using the differences between the positions and/or orientations of the one or more features and/or targets to determine the translations, scales, and/or rotations between the intra-operative patient coordinate system and the articulated arm coordinate system. The translations, scales, and/or rotations may be used to determine the patient to computer-assisted medical device kinematic relationship. In some examples, the patient to computer-assisted medical device kinematic relationship may be used to transform the target selected during process 410 and/or the one or more no-fly zones selected during process 415 from the intra-operative patient coordinate system to the articulated arm coordinate system. In some examples, additional coordinate systems (e.g., coordinates systems 320, 325, 330, and/or 335) and their kinematic relationships (e.g., kinematic relationships 370, 372, 374, and/or 380) may be used to transform the target selected during process 410 and/or the one or more no-fly zones selected during process 415 from the intra-operative patient coordinate system to one or more of the additional coordinate systems.

At a process 440, a medical tool insertion path and pose is determined. In some embodiments, once the computer-assisted medical device is registered to the patient during process 435, the insertion path and the pose of the medical tool to be used during the medical procedure may be determined. In some examples, the various kinematic relationships of the computer-assisted medical device (e.g., kinematic relationships 370, 372, 374, and/or 380) along with the patient to computer-assisted medical device kinematic relationship may be used to determine an insertion path and a pose for the medical tool that aligns the tool with the target selected during process 410 and allows insertion of the medical tool along the insertion path and toward the target without intersecting any of the one or more no-fly zones determined during process 415. In some examples, determination of the medical tool insertion path and pose may further include determining a position and/or orientation of a guide hole of a tool guide, such as guide hole 120 of tool guide 100, and/or desired joint positions for the articulated arms of the computer-assisted medical device that are used to hold the tool guide. In some examples, determination of the medical tool insertion path and pose may be an iterative process in which a proposed medical tool insertion path and pose are shown to medical personnel with the medical personnel being able to make adjustments to the insertion path and/or pose. In some examples, the proposed medical tool insertion path and pose may be shown to the medical personnel as an overlay on the one or more intra-operative images obtained during process 425, the one or more pre-operative images loaded during process 405, and/or the one or more computer-assisted medical device based images obtained during process 435.

At a process 445, the articulated arms that are used to hold the tool guide are deployed. In some examples, positioning and/or orientation of the articulated arms that are used to hold the tool guide may be a complex task that may not be practical either by manual manipulation of the articulated arms in a clutched mode and/or via teleoperation. In some examples, the computer-assisted medical system may plan and execute motion plans for the articulated arms that are used to hold the tool guide so as to place them in a suitable position and/or orientation for attaching the tool guide. In some examples, the suitable position and/or orientation may be approximately located where the tool guide is to be positioned and/or oriented as determined during process 440. In some examples, the suitable position and/or orientation may be somewhat farther apart than the actual size of the tool guide to allow for extra clearance between the distal ends of the articulated arms that are to receive the mounting arms of the tool guide, such as the mounting arms 140 of tool guide 100. In some examples, the deployment plan may further include determining one or more collision avoidance paths with other articulated arms of the computer-assisted medical device (e.g., the articulated arm to which the imaging device of process 435 is mounted), the set-up structure of the computer-assisted medical device, the patient, and/or the like. In some examples, the deployment plan may also include planned motions to move the other articulated arms and/or the set-up structure of the computer-assisted medical device out of the way of the articulated arms that are holding the tool guide. In some examples, during deployment, forces and/or torques in the articulated arms may be monitored in order to detect unforeseen collisions with other objects, personnel, and/or the like in the vicinity of the computer-assisted medical device. In some examples, the deployment may include activating one or more actuators in the articulated arms and/or the set-up structure of the computer-assisted medical device by controlling one or more voltages, currents, duty cycles, and/or the like. In some examples, the deployment may be triggered by medical personnel using an activation button located on one of the articulated arms, via an operator workstation, and/or the like.

At a process 450, the tool guide is attached. In some embodiments, each of the mounting arms of the tool guide is mounted on a distal end of a corresponding one of the articulated arms. In some examples, the attaching of the tool guide may include inserting one or more flanges, pins, and/or the like into corresponding receiving notches, holes, and/or the like on the articulated arms. In some examples, the attaching of the tool guide may include one or more medical personnel manually moving the tool guide and/or the articulated arms. In some examples, the articulated arms may be placed in a clutched and/or unlocked state to allow manual movement of the joints of the articulated arm, and/or may be placed in a resistive state allowing the joints of the articulated arms to be moved, but with some resistance so as to avoid excessive movement of the articulated arms.

At an optional process 455, the tool guide is initially placed. In some embodiments, once the computer-assisted medical device detects the attachment of an appropriate tool guide (e.g., using the identifying features of the tool guide), the articulated arms holding the tool guide may be placed in a special clutched mode. In some examples, when one of the articulated arms holding the tool guide is placed in a clutched mode by the medical personnel, that articulated arm may be manually moved by the medical personnel. To avoid placing undue strain on the tool guide and the articulated arms, the articulated arm holding the other end of the tool guide may be placed in a following mode where one or more joint actuators of the articulated arm holding the other end of the tool guide are driven based on the constrained kinematics of the tool guide and the closed kinematic loop including the tool guide and the two articulated arms holding the tool guide. In some examples, a position and/or orientation of a gantry of the computer-assisted medical device may be adjusted based on manual movement imposed by the medical personnel so that each of the articulated arms may be moving at the same time. In some examples, one or more forces and/or torques in the articulated arms holding the tool guide may also be monitored to reduce force and/or torque detected during process 455. In some examples, when the joints of the tool guide include one or more actuators, these one or more actuators may also be driven during process 455. In some examples, the various kinematic relationships and corresponding Jacobian transposes may be used to convert the observed forces and/or torques into position and/or orientation adjustments of the one or more joint actuators.

At a process 460, the tool guide is placed. Based on the medical tool insertion path and pose determined during process 440, the tool guide is placed so that the guide hole of the tool guide is positioned and/or oriented in alignment with the medical tool insertion path and located at as suitable distance from the target. In some examples, the suitable distance may be determined based on a length of the medical tool to be used with the tool guide and/or to provide a stop that may limit a distance along which the medical tool may be inserted toward the target.

In some embodiments, the tool guide may be placed semi-automatically under the direction of medical personnel. In some examples, a special clutching mode, similar to the clutching mode used during process 455 may be used during the semi-automatic placement. To aid the medical personnel with the placement, the computer-assisted medical device may overlay one or more visual cues on images showing the computer-assisted medical device and/or the patient. In some examples, the one or more visual cues may depict a conical and/or other shape converging to the desired position and/or orientation for the tool guide. In some examples, the visual cues may include depiction of a virtual rendition of the medical tool and a desired position and/or orientation of the medical tool. In some examples, haptic feedback may be used to direct the tool guide to the desired position and/or orientation. In some examples, when the joints of the tool guide include one or more actuators, these one or more actuators may also be driven during process 460.

In some embodiments, the tool guide may be placed automatically. In some examples, constrained trajectory planning between the two articulated arms may be used to automatically direct the tool guide to the desired position and/or orientation. In some examples, the constrained trajectory planning may include planning a trajectory for one of the arms holding the tool guide and placing the other articulated arm holding the tool guide in the special clutching mode described during process 455 using following and/or force and/or torque reduction. In some examples, when the joints of the tool guide include one or more actuators, these one or more actuators may also be driven during process 460. In some examples, the automatic placement may support a manual override control that allows medical personnel to abort the automatic placement.

At a process 465, the articulated arms holding the medical tool are locked. Once the tool guide is placed during process 460, it is ready for use by medical personnel. To avoid changes in the position and/or orientation of the tool guide and the guide hole, the joints of the articulated arms holding the tool guide may be locked. In some examples, the joints may be locked using one or more braking mechanisms that resist motion in the articulated arms. In some examples, the active joints of the articulated arms holding the tool guide may also be driven to maintain the desired position and/or orientation of the tool guide and the guide hole.

At a process 470, the medical tool is placed in the tool guide. Once the tool guide and the guide hole are placed and aligned to the target during process 465, medical personnel may insert the appropriate medical tool through the guide hole.

At a process 475, the medical tool is advanced to the target. Once the medical tool is placed in the tool guide during process 470, the medical tool may be advanced to the target. In some examples, the medical tool may be advanced through the guide hole until it reaches the target.

At a process 480, a procedure is performed. Once the medical tool has reached the target during process 475, it is ready for use. In some examples, the use may include percutaneous ablation including RF, cryo, microwave, and/or other forms of ablation), percutaneous needle biopsy, bone drilling, pedicle screw placement, seed planting, marker placement, medicine delivery, high magnification imaging, micro surgery, and/or the like. In some examples, the tool guide may be actively moved in synchronization with a physiological motion of the patient such as the physiological motions associated with respiration, heart beats, and/or the like in order to maintain the tool guide and the guide hole aligned with and/or at a desired distance from the target. In some examples, images captured from an imaging device, such as imaging device 270, may be used to detect the physiological motion by noting changes in position and/or orientation of one or more markers associated with the patient. In some examples, the detected physiological motion may be used to detect changes in the patient to computer-assisted medical device kinematic relationship, which may be used as feedback to adjust one or more of the actuators in the articulated arms and/or end effectors holding the tool guide to maintain a constant tool guide to patient kinematic relationship.

In some embodiments, portions of the method 400 may be repeated as appropriate. In some examples, one or more of the processes 405-480 may be repeated to change the target, switch medical tools, switch tool guides, and/or the like.

As discussed above and further emphasized here, FIG. 4 is merely an example, which should not unduly limit the scope of the claims. One of ordinary skill in the art would recognize many variations, alternatives, and modifications. According to some embodiments, additional control approaches may also be supported by the computer-assisted medical device while working with a tool guide. In some examples, the computer-assisted medical device may monitor the patient table to allow for changes in position and/or orientation of the patient table. In some examples, the computer-assisted medical device may monitor the state of the table to medical device kinematic relationship (e.g., table to device-base kinematic relationship 365) and adjust the other kinematic relationships (e.g., kinematic relationships 370, 372, 374, 376, and/or 378) in order to keep the tool guide to patient kinematic relationship constant and/or to automatically account for the movement of the patient table. In some examples, this monitoring may allow for automated adjustment of the tool guide without repeating processes 435-475).

In some embodiments, any of processes 470, 475, and/or 480 may be performed automatically. In some examples, the medical tool may be an end effector of an additional articulated arm of the computer-assisted medical device. In some examples, the additional articulated arm may be used to place the medical tool (i.e., the additional articulated arm's end effector) in the tool guide, advance the medical tool to the target, and/or perform the procedure. In some examples, a tool guide with a different configuration than tool guide 100 may be more suitable for automating processes 470, 475, and/or 480 using the additional articulated arm.

Figure 5A:
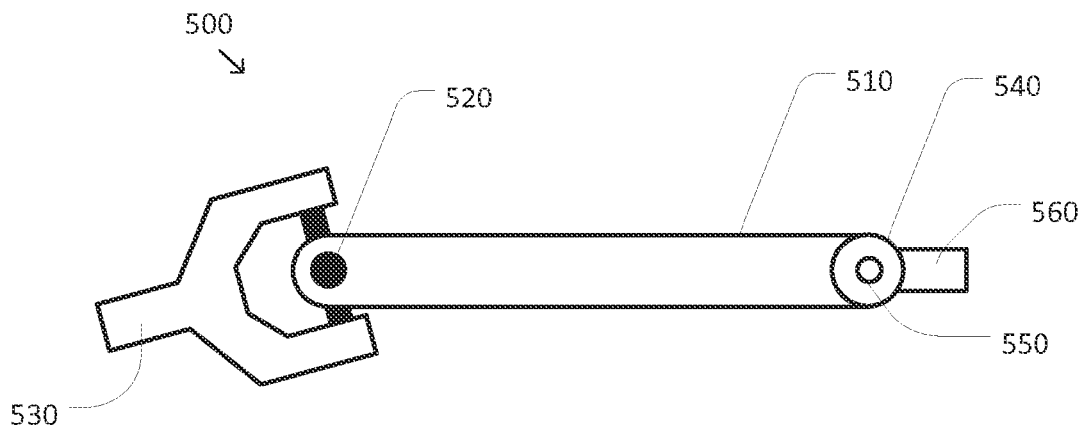
FIGS. 5A and 5B are simplified diagrams of a top and side view of another tool guide for use with two articulated arms and/or end effectors according to some embodiments.
Figure 5B:
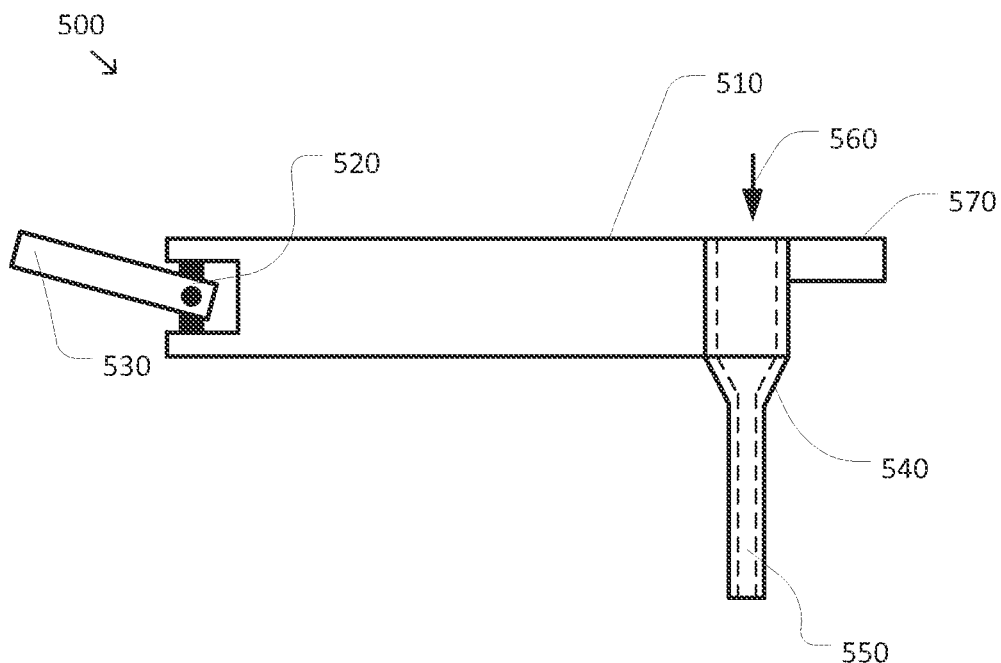

FIGS. 5A and 5B are simplified diagrams of a top and side view of another tool guide 500 for use with two articulated arms and/or end effectors according to some embodiments. As shown in FIGS. 5A and 5B, tool guide 500 includes a rigid or mostly rigid body 510 with an elongated shape. At a first end of body 510, tool guide 500 includes a joint 520 that couples body 510 to a mounting arm 530. In some examples, joint 520 and mounting arm 530 may be similar to the joints 130 and mounting arms 140. As further shown in FIGS. 5A and 5B, the joint 520 includes a two degree of freedom universal joint allowing independent rotation of mounting arm 530 relative to body 510 along two separate axes. In some examples, the inclusion of joint 520 adds additional degrees of freedom to a closed kinematic chain including tool guide 500. In some examples, these additional degrees of freedom may provide greater flexibility in positioning the articulated arm and/or end effector that is holding tool guide 500. And although FIGS. 5A and 5B depict joint 520 as a two degree of freedom universal joint, other configurations are possible. In some examples, joint 520 may be a ball-in-socket joint. In some examples, joint 520 may include zero and/or one degree of freedom and/or may include a more complex arrangement of joints and links providing more than two degrees of freedom. In some examples, joint 520 may be passive, may include varying levels of resistance to motion, and/or may include one or more actuators making joint 520 an active joint. In some embodiments, joint 520 may include one or more sensors for determining a position, orientation, force, and/or torque of joint 520. In some embodiments, joint 520 may include one or more sensors for determining a position, orientation, force, and/or torque of joint 520. In some examples joint 520 may be lockable (e.g., by a manually-tightened friction feature) to temporarily prevent joint 520 from moving. In some embodiments, joint 520 may benefit from a variable stiffness joint mechanism using materials and techniques such as electro-rheological (ER) and/or magneto-rheological (MR) fluids.

In some embodiments, mounting arm 530 may include one or more features to help support use of tool guide 500 with the articulated arm and/or end effector. In some examples, the end of mounting arm 530 opposite joint 520 may include a standardized attachment arrangement designed to mate with specific articulated arms and/or end effectors. In some examples, the standardized attachment may provide a rigid, non-slip attachment between tool guide 500 and the articulated arms and/or end effectors. In some examples, mounting arm 530 may include one or more notches, flanges, clips, and/or the like suitable for attaching mounting arm 530 to an articulated arm and/or end effector. In some examples, by attaching tool guide 500 to the articulated arm using mounting arm 530, tool guide 500 becomes an end effector for the articulated arm. In some examples, mounting arm 530 may include suitable identifying features so the articulated arm and/or end effector to which mounting arm 530 is attached may identify mounting arm 530 as belonging to tool guide 500 and may further identify a model number of tool guide 500. In some examples, the identifying features may include one or more physical patterns, electrical contacts, magnets, RFID devices, and/or the like. In some examples, mounting arm 530 may further include electrical and/or physical contacts for allowing the articulated arms and/or end effectors to read the sensors and/or command the actuators in the joint 520.

In contrast to tool guide 100, which has guide hole 120, second joint 130, and second mounting arm 140, tool guide 500 includes a tool sleeve 540 at a second end of the body 510 opposite joint 520 and mounting arm 530. Tool sleeve 540 includes a shaft with a hole 550 along its length through which a medical tool is inserted in the direction of arrow 560. In some examples, tool sleeve 540 may have a tapered portion that may help align the medical tool while it is being inserted into tool sleeve 540 and which may also act as a stop to prevent further insertion of the medical tool when a wider upper portion with a matching taper on the medical tool reaches the tapered portion. In some examples, the tool sleeve may be detachable, such as with a snap fit, to allow different tool sleeves with different lengths, diameters, and/or tapered profiles to be used with tool guide 540. In some examples, tool sleeve 540 may be designed to have a standardized size and profile to be used with commonly used end effectors of a computer-assisted medical device, such as the computer-assisted medical device described in FIG. 2. In some examples, tool sleeve 540 may be a cannula designed to be inserted at a site on a patient where an incision has been made.

In some embodiments, tool sleeve 540 may be associated with a mount 570. Similar to the mounting arm 530, mount 570 may include a standardized attachment arrangement designed to mate with specific articulated arms and/or end effectors. In some examples, the standardized attachment may provide a rigid, non-slip attachment between tool guide 500 and the articulated arms and/or end effectors. In some examples, mount 570 may include one or more notches, flanges, clips, and/or the like suitable for attaching mount 570 to an articulated arm and/or end effector. In some examples, mount 570 may be designed to rigidly attach tool guide 500 to an articulated arm and/or end effector while still permitting the articulated arm and/or end effector to operate the medical tool inserted in tool sleeve 540. In some examples, mount 570 may include suitable identifying features so the articulated arm and/or end effector to which mount 570 is attached may identify mount 570 as belonging to tool guide 500 and may further identify a model number of tool guide 500. In some examples, the identifying features may include one or more physical patterns, electrical contacts, magnets, RFID devices, and/or the like.

In some embodiments, tool guide 500 may further include a memory device (not shown). In some examples, the memory device may be used to store information associated with tool guide 500 including tool guide type, tool guide identification number, tool guide model number, tool guide kinematic parameters, and/or the like. In some examples, the stored information may be read by the computer-assisted system upon connection of either the mounting arm 530 and/or the mount 570 to one of the articulated arms and/or one of the end effectors. In some examples, the read information may be used by the computer-assisted system to identify tool guide 500, set control parameters, access the kinematic parameters, and/or the like. In some examples, the memory device may be accessed using the electrical contacts, RF communication, and/or the like. In some examples, the memory device may be accessed using the electrical contacts, RF communication, and/or the like. In some examples, the memory device may include a machine readable media, such as RAM, PROM, EPROM, FLASH-EPROM, any other memory chip or cartridge, and/or any other medium from which a processor or computer is adapted to read.

In some embodiments, mounting arms 530 and/or mount 570 may be used to provide electrical power to tool guide 500. In some examples, the electrical power may be used to operate the sensors, drive the actuators, control stiffness of the joint 520 via ER and/or MR fluids, and/or the like.

In some embodiments, tool guide 500 may be designed to be used where the medical tool inserted into tool sleeve 540 is an end effector mounted on the distal end of an articulated arm. That is, in some configurations tool guide 500 is mounted to a first and second arm via mounting arm 530 and mount 570 respectively, a medical tool is attached to the second arm holding mount 570, and the medical tool is inserted through the tool sleeve 540 so that the first arm supports the tool sleeve 540 mounted to the second arm. In some examples, tool guide 500 may provide the same advantages as tool guide 100 including improved rigidity, stiffness, and vibration resistance while one of the articulated arms holding the tool guide is also used to hold and actuate the medical tool inserted into tool sleeve 540.

In some embodiments, tool guide 500 may be used in place of tool guide 100 while performing method 400 with little or no modification. The tool sleeve 540 may be inserted through an incision in the patient while the first articulated arm is placed in a clutched mode. A second articulated arm may then be deployed near mounting arm 530 by using the kinematic relationships of the first articulated arm and tool guide 500. A process similar to process 440 may then be used to attach mounting arm 530 to the second articulated arm. In some examples, tool guide 500 may then be further placed using a process similar to process 460. In some examples, medical personnel may then operate the medical tool end effector with the second articulated arm being placed in a following mode, similar to the following modes of process 455 and/or 460, where the second articulated arm helps adjust a position and orientation of tool guide 500 and tool sleeve 540 to support the desired motions of the medical tool while also steadying the first articulated arm and/or reducing vibration in the medical tool.

As discussed above and further emphasized here, FIGS. 1 and 5 are merely examples which should not unduly limit the scope of the claims. One of ordinary skill in the art would recognize many variations, alternatives, and modifications. According to some embodiments, additional configurations are possible for tool guides 100 and/or 500. In some examples, guide hole 120 of tool guide 100 may be replaced with a tool sleeve similar to tool sleeve 540 to better support use of a tool guide held by two articulated arms and providing support for a medical tool operated by a third articulated arm. In some embodiments, haptic feedback may be employed whenever medical personnel are manipulating the medical tool.

Some examples of control units, such as control unit 280 may include non-transient, tangible, machine readable media that include executable code that when run by one or more processors (e.g., processor 285) may cause the one or more processors to perform the processes of method 400. Some common forms of machine readable media that may include the processes of method 400 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A method of controlling motion of a medical tool, the method comprising:
   determining an insertion path and a pose for the medical tool based on a target;
   deploying first and second articulated arms of a computer-assisted medical device so that a distal end of each of the first and second articulated arms are positioned and oriented relative to each other based on a size and a shape of a tool guide, the first and second articulated arms being positionable independently of each other with respect to a base, wherein the first articulated arm comprises a plurality of first moveable links actuated by at least one first actuator and forming a first kinematic chain extending from the base, wherein the second articulated arm comprises a plurality of second moveable links actuated by at least one second actuator and forming a second kinematic chain extending from the base;
   receiving the tool guide for coupling with the first articulated arm and with the second articulated arm using respective mounting arms of the tool guide such that the tool guide functions as a link in a closed kinematic loop formed by joining the first kinematic chain to the second kinematic chain;
   orienting, by operation of the at least one first actuator and/or the at least one second actuator, a guide hole of the tool guide so as to align the guide hole with the insertion path;
   positioning, by operation of the at least one first actuator and/or the at least one second actuator, the guide hole a desired distance away from the target based on the pose;
   receiving the medical tool in the guide hole; and
   advancing the medical tool along the insertion path and toward the target.

2. The method of claim 1, further comprising locking joints of the first and second articulated arms after orienting and positioning the guide hole and before placing the medical tool in the guide hole.

3. The method of claim 1, further comprising determining a kinematic relationship between the first and second articulated arms using constrained kinematics of the tool guide.

4. The method of claim 1, wherein receiving the tool guide comprises placing the first articulated arm in a clutched mode.

5. The method of claim 1, wherein orienting and positioning the guide hole comprises planning and executing a trajectory for the first articulated arm and placing the second articulated arm in a following mode.

6. The method of claim 1, further comprising using a body of the tool guide as a stop for the medical tool.

7. The method of claim 1, receiving identifying information from the tool guide.

8. The method of claim 1, wherein the medical tool is adapted for use during one or more medical procedures selected from a group consisting of percutaneous ablation, percutaneous needle biopsy, bone drilling, pedicle screw placement, seed planting, marker placement, medicine delivery, high magnification imaging, and micro surgery.

9. The method of claim 1, further comprising registering a patient with the computer-assisted medical device to determine a kinematic relationship between the target and the computer-assisted medical device.

10. The method of claim 9, wherein registering the patient with the computer-assisted medical device comprises obtaining one or more images of the target with an imaging device.

11. The method of claim 10, wherein the imaging device is mounted on a third articulated arm of the computer-assisted medical device and the method further comprises positioning and orienting the imaging device.

12. The method of claim 1, wherein orienting the guide hole of the tool guide and positioning the guide hole a desired distance away from the target comprises placing the first articulated arm in a clutched mode and operating the second articulated arm in a following mode.

13. The method of claim 12, wherein the following mode comprises driving the at least one second actuator based on kinematics of the first articulated arm and constrained kinematics of the tool guide.

14. The method of claim 12, wherein the following mode comprises driving the at least one second actuator in order to reduce force or torque in the second articulated arm.

15. The method of claim 12, further comprising providing one or more visual cues to an operator to facilitate the orienting and positioning.

16. The method of claim 12, further comprising providing haptic feedback to an operator to facilitate the orienting and positioning.

17. A non-transitory machine-readable medium comprising a plurality of machine-readable instructions which when executed by one or more processors associated with a medical device are adapted to cause the one or more processors to perform a method comprising:
   determining an insertion path and a pose for a medical tool based on a target;
   deploying first and second articulated arms of a computer-assisted medical device so that a distal end of each of the first and second articulated arms are positioned and oriented relative to each other based on a size and a shape of a tool guide, the first and second articulated arms being positionable independently of each other with respect to a base, wherein the first articulated arm comprises a plurality of first moveable links actuated by at least one first actuator and forming a first kinematic chain extending from the base, wherein the second articulated arm comprises a plurality of second moveable links actuated by at least one second actuator and forming a second kinematic chain extending from the base;

receiving the tool guide for coupling with the first articulated arm and with the second articulated arm using respective mounting arms of the tool guide such that the tool guide functions as a link in a closed kinematic loop formed by joining the first kinematic chain to the second kinematic chain;

orienting, by operation of the at least one first actuator and/or the at least one second actuator, a guide hole of the tool guide so as to align the guide hole with the insertion path;

positioning, by operation of the at least one first actuator and/or the at least one second actuator, the guide hole a desired distance away from the target based on the pose;

placing the medical tool in the guide hole; and advancing the medical tool along the insertion path and toward the target.

18. The non-transitory machine-readable medium of claim 17, wherein the method further comprises registering a patient with the computer-assisted medical device to determine a kinematic relationship between the target and the computer-assisted medical device.

19. The non-transitory machine-readable medium of claim 17, wherein orienting and positioning the guide hole comprises placing the first articulated arm in a clutched mode and operating the second articulated arm in a following mode.

20. The non-transitory machine-readable medium of claim 17, wherein the method further comprises providing haptic feedback to an operator to facilitate the orienting and positioning.

* * * * *